(12) United States Patent
Nelson

(10) Patent No.: US 6,303,132 B1
(45) Date of Patent: Oct. 16, 2001

(54) ADMINISTERING PROGESTERONE USING EMU OIL

(76) Inventor: Ardell H. Nelson, Canyon Ranch, Highway 187, Vanderpool, TX (US) 78885

( * ) Notice: Subject to any disclaimer, the term of this patent is extended or adjusted under 35 U.S.C. 154(b) by 0 days.

(21) Appl. No.: 09/354,836

(22) Filed: Jul. 16, 1999

(51) Int. Cl.[7] ................ A61K 9/00; A61K 6/00
(52) U.S. Cl. ............. 424/400; 424/401; 514/947
(58) Field of Search .................. 424/400, 401; 514/947

(56) References Cited

U.S. PATENT DOCUMENTS

| | | | |
|---|---|---|---|
| 4,150,128 * | 4/1979 | Jasionowski | 424/240 |
| 5,431,924 | 7/1995 | Ghosh et al. | 424/522 |
| 5,472,713 | 12/1995 | Fein et al. | 424/522 |
| 5,626,882 | 5/1997 | Marrone et al. | 424/522 |
| 5,662,921 | 9/1997 | Fein et al. | 424/436 |
| 5,677,338 | 10/1997 | Manker et al. | 514/547 |
| 5,688,746 | 11/1997 | Thacker | 508/101 |
| 5,698,227 | 12/1997 | Rivlin | 424/522 |
| 5,725,858 | 3/1998 | Fioretti et al. | 424/192.1 |
| 5,744,128 * | 4/1998 | Holick | 424/60 |
| 5,747,659 | 5/1998 | Fioretti et al. | 536/23.4 |
| 5,786,179 | 7/1998 | Kousoulas et al. | 435/69.7 |
| 5,801,196 | 9/1998 | Manker et al. | 514/547 |
| 5,849,334 | 12/1998 | Rivlin | 424/522 |
| 5,929,113 | 7/1999 | Manker et al. | 514/547 |
| 6,056,972 * | 5/2000 | Hermsmeyer | 424/449 |

* cited by examiner

Primary Examiner—Thurman K. Page
Assistant Examiner—S. Tran
(74) Attorney, Agent, or Firm—Morrison & Foerster LLP

(57) ABSTRACT

A topical progesterone composition contains a concentration of progesterone and a concentration of emu oil. The emu oil acts as a transdermal vehicle to quickly and efficiently carry the progesterone into the body.

16 Claims, 1 Drawing Sheet

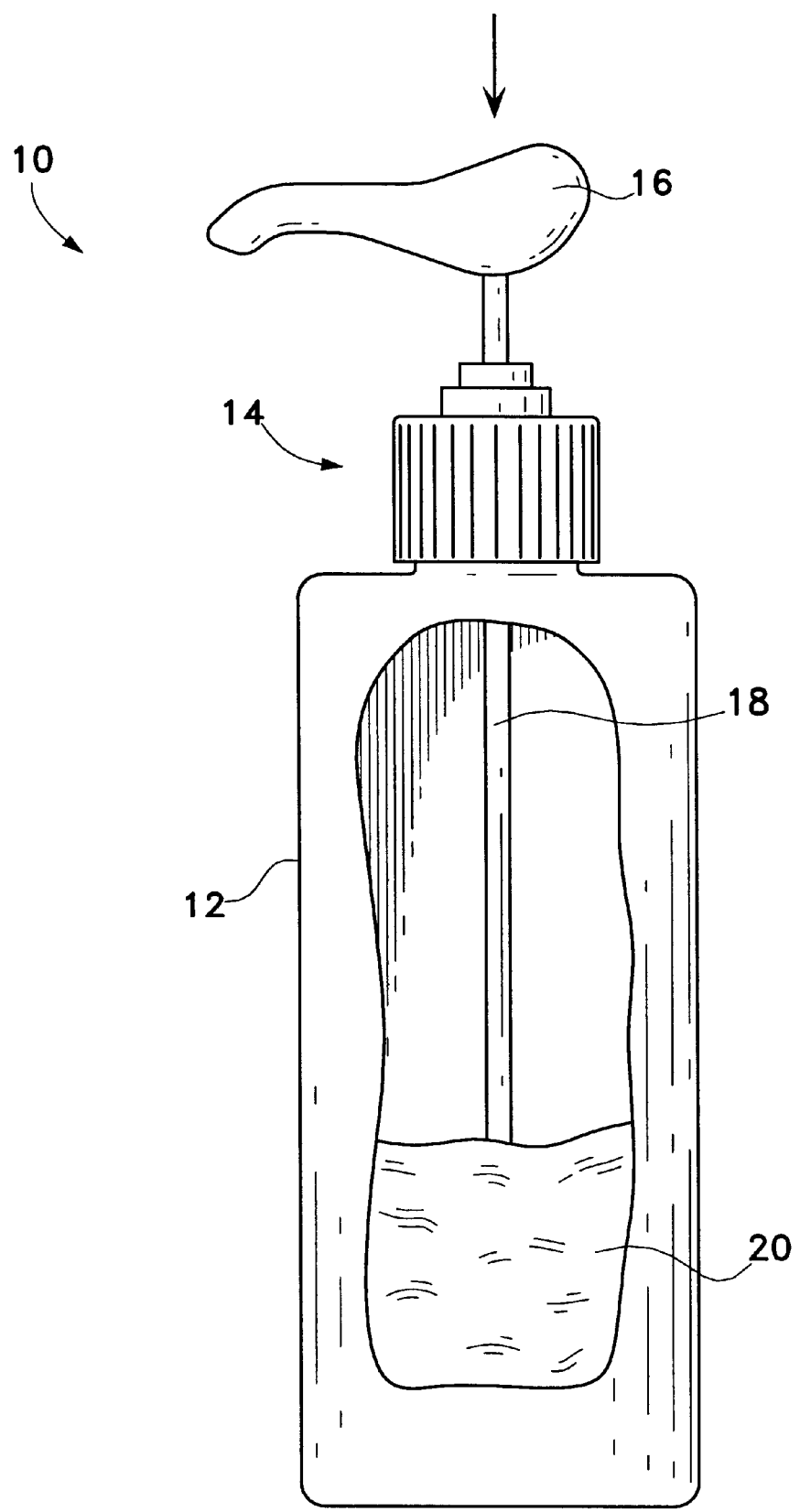

ADMINISTERING PROGESTERONE USING EMU OIL

This invention relates to a method of using emu oil to topically administer progesterone and to a progesterone composition including emu oil which may be applied to the surface of the skin to facilitate delivery of the progesterone.

BACKGROUND OF THE INVENTION

Natural progesterone is a hormone produced by both women and men, although to a lesser extent in men, and is an important precursor in the biosynthesis of other hormones in the human body. The use of natural progesterone has been linked to the relief of hot flashes, mood swings, bloating, loss of libido, vaginal dryness, and other uncomfortable symptoms associated with menopause and pre-menstrual syndrome (PMS). It is also useful in counteracting the damaging effects of estrogen dominance. Natural progesterone attaches to and blocks the receptors for estrogen molecules and estrogen-like compounds, causing them to travel through the body and eventually to be metabolized and excreted in urine. Natural progesterone also has been shown to alleviate, prevent, or even actually reverse osteoporosis.

Natural progesterone typically is taken orally as a capsule or tablet. While this form has the advantage of being very convenient, absorption of the progesterone via the digestive tract is very inefficient because 85–90% of the progesterone will be metabolized immediately by the liver and excreted in bile. When taken orally, the progesterone, like other fat-soluble nutrients, is taken up by the portal vein and transported directly to the liver where much of it is metabolized and conjugated for excretion. As a result, the amount of ingested progesterone required to be effective may be up to 10–25 times higher than if the progesterone is absorbed directly into the body via the skin. Large doses of oral progesterone may have negative side effects, including elevated levels of metabolites and unnecessary liver stress.

Topically applied progesterone creams or lotions do not contain as large an amount of progesterone because it may be absorbed directly by the body. The cream or lotion usually contains one or more transdermal carriers that carry the progesterone through the skin into the fatty tissues where the progesterone may be absorbed naturally into the bloodstream. The specific transdermal carrier is very important because some carriers (such as mineral oil) will cause the progesterone to decompose while on the surface of the skin, thus reducing or losing its effectiveness. Carriers that have slow transdermal penetration rates may require higher concentrations of progesterone to achieve sufficient progesterone absorption. In addition, most creams stay on the skin surface for a prolonged period of time, thus making use inconvenient. It is generally desirable to have a cream or lotion that is substantially absorbed by the skin very quickly, e.g., 30 seconds or less.

SUMMARY OF THE INVENTION

In general, in one aspect, the invention relates to a progesterone composition comprising a concentration of natural progesterone and a concentration of emu oil.

In general, in another aspect, the invention relates to a method of topically administering a progesterone composition. The method comprises applying to the skin surface a composition containing a concentration of progesterone and a concentration of emu oil.

In general, in another aspect, the invention relates to a dispenser for dispensing a topically administered progesterone composition, comprising a container body having the progesterone composition disposed therein. The composition comprises a concentration of progesterone and a concentration of emu oil.

Advantages of the invention include high transdermal penetration rate for efficient delivery of progesterone into the body. Other advantages of the invention will become apparent from the following description and the claims.

BRIEF DESCRIPTION OF THE DRAWINGS

FIG. 1 is a cut-away view of a progesterone cream dispensing unit.

DETAILED DESCRIPTION OF THE PREFERRED EMBODIMENTS

It should be noted that the specific process steps of making therapeutic emulsions in cream or lotion form are well-known to one having ordinary skill in the art and will not be described in detail herein. Suffice it to say, only those details which are necessary to practice the invention will be discussed.

As alluded to previously, it is important for topical progesterone creams or lotions to be quickly and efficiently absorbable into the body. Emu oil, in addition to having a number of well-documented health benefits (see, e.g., U.S. Pat. No. 5,662,921: "Therapeutic Uses of Emu Oil"), is also a very efficient transdermal vehicle which does not promote decomposition of progestrone. The present invention combines natural progesterone with emu oil to achieve a progesterone composition which is quickly and efficiently absorbable into the body.

In one embodiment, the progesterone and emu oil are thoroughly mixed with water and an ordinary emulsifying agent to form a cream. Although emu oil and progesterone alone are sufficient for effective treatment, these two ingredients by themselves can be somewhat inconvenient under certain circumstances, for example, when one wants to get dressed quickly after applying the progesterone. When convenience is not a problem, the simple emu oil and progesterone combination will work very well and also may have the beneficial effect of conditioning the skin.

The amount of progesterone used may be any amount that is effective for treating the desired symptoms, but preferably enough progesterone is used to constitute 400–500 mg of progesterone per ounce-weight of cream. A higher concentration of progesterone will result in more progesterone delivered to the body per unit of cream applied, likewise, a lower concentration will result in less progesterone delivered. Similarly, the amount of emu oil used may be any amount that will achieve the desired transdermal penetration rate, but preferably enough emu oil is used such that the emu oil constitutes 3–4% by weight of the cream. This percentage range has been found to provide optimal transdermal penetration for the amount of emu oil used, but a percentage range of 2–10% by weight has also been found to be effective.

It is preferred that natural progesterone be used, i.e., progesterone that is bio-identical to progesterone produced by the human body such as U.S.P. Natural Progesterone (micronized) because of the health benefits which may be derived therefrom as previously explained. The invention may, however, be practiced using either natural or synthetic progesterone (such as progestin) which has a man-made molecular structure similar to natural progesterone.

The emu oil may be any commercially available emu oil, but in a preferred embodiment, pure emu oil which has been processed at temperatures not exceeding 300 degrees Fahrenheit is used. It is also preferable that the emu oil be held at about 300 degrees Fahrenheit for at least five hours in order to completely sterilize the oil. Emu oil which has been heated to temperatures in excess of 300 degrees Fahrenheit may still be used, but may contain undesirable by-products as a result of the excessive heating.

Although the main ingredients of the invention are progesterone and emu oil, other ingredients may certainly be added to enhance the therapeutic and other beneficial properties of the cream. For example, in one embodiment, one or more of the following ingredients may be added in various amounts to the cream to enhance the benefits of the cream: evening primrose oil; black cohosh; licorice; dong quai extracts; allantoin; ginko biloba; and vitamins A, B-5, C, D or E, or combinations thereof.

The cream may be applied to the skin surface as often and in any dosage as may be necessary for effective treatment of symptoms. In a preferred embodiment, the cream is applied twice a day to a thin-skin body area (such as on the underarm), and in a dosage that will deliver 10–12 mg of progesterone per application. For relief of symptoms caused by PMS and menopause, it is recommended that the above frequency and dosage be continued for 14 and 21 consecutive days, respectively. Because hormone levels can fluctuate considerably from individual to individual, the dosage may be adjusted as needed for effective relief.

In one embodiment, the progesterone cream is packaged in a convenient dispenser such as a pump bottle, shown in FIG. 1. The pump bottle 10 has a hollow, cylindrical container 12 and a pump assembly 14 attach thereto. The pump assembly 14 includes a dispenser head 16 and a tube 18 which extends into a portion of progesterone cream 20 disposed in the container 12. To accurately dispense a predetermined amount of the progesterone cream 20 from the container 12, one simply pushes down on the dispenser head 16 as shown by the arrow.

The following experiment illustrates the superior transdermal penetration rate of progesterone cream containing emu oil compared to the same progesterone cream without emu oil. Progesterone cream having 500 mg of progesterone per ounce-weight, but without emu oil, was topically applied to six test subjects twice a day (20–24 mg of progesterone per day) for 14 consecutive days. The subjects' progesterone levels were monitored by saliva hormone assay. The same progesterone cream, but with 3–4% by weight of emu oil, was then similarly applied to the same six test subjects for 14 days and the progesterone levels monitored using saliva hormone assay. The results showed that the levels of progesterone of the six subjects were markedly higher when progesterone cream containing emu oil was used.

It is to be understood that the embodiments described herein are illustrative only, and that other embodiments may be derived by one having ordinary skill in the art without departing from the scope of the invention. For example, although only one type of dispenser was shown, other suitable types of dispensers or containers may certainly be used such as jars, squeeze bottles, tubes, roll-ons, etc. Accordingly, the scope of the invention should be limited only by the following claims.

What is claimed is:

1. A topically administered progesterone composition, comprising:
    a concentration of progesterone; and
    a concentration of emu oil.

2. The composition of claim 1, wherein the concentration of progesterone is approximately 400–500 milligrams per ounce-weight of the composition.

3. The composition of claim 1, wherein the progesterone is a natural progesterone.

4. The composition of claim 1, wherein the emu oil comprises approximately 3%–4% by weight of the composition.

5. The composition of claim 1, wherein the emu oil comprises approximately 2%–10% by weight of the composition.

6. A method of topically administering a progesterone composition, comprising:
    applying to a skin surface a composition comprising a concentration of progesterone and a concentration of emu oil.

7. The method of claim 6, wherein the concentration of progesterone is approximately 400–500 milligrams per ounce-weight of the composition.

8. The method of claim 6, wherein the progesterone is a natural progesterone.

9. The method of claim 6, wherein the emu oil comprises approximately 3%–4% by weight of the composition.

10. The method of claim 6, wherein the emu oil comprises approximately 2%–10% by weight of the composition.

11. A dispenser for dispensing a topically administered progesterone composition, comprising:
    a container body having a progesterone composition disposed therein, the composition comprising a concentration of progesterone and a concentration of emu oil.

12. The dispenser of claim 11, further comprising means on the container for dispensing the progesterone composition.

13. The dispenser of claim 11, wherein the concentration of progesterone is approximately 400–500 milligrams per ounce-weight of the composition.

14. The dispenser of claim 11, wherein the progesterone is a natural progesterone.

15. The dispenser of claim 11, wherein the emu oil comprises approximately 3%–4% by weight of the composition.

16. The dispenser of claim 11, wherein the emu oil comprises approximately 2%–10% by weight of the composition.

* * * * *